United States Patent [19]

Kuekenhoehner et al.

[11] Patent Number: 5,001,242

[45] Date of Patent: Mar. 19, 1991

[54] PROCESS FOR THE PREPARATION OF 4-METHYLENETETRAHYDROPYRAN

[75] Inventors: Thomas Kuekenhoehner, Frankenthal; Wolfgang Spiegler; Norbert Goetz, both of Worms; Wolfgang Rohr, Wachenheim, all of Fed. Rep. of Germany

[73] Assignee: BASF Aktiengesellschaft, Ludwigshafen, Fed. Rep. of Germany

[21] Appl. No.: 547,193

[22] Filed: Jul. 3, 1990

[30] Foreign Application Priority Data

Aug. 8, 1989 [DE] Fed. Rep. of Germany ....... 3926170

[51] Int. Cl.$^5$ ............................................ C07D 309/00
[52] U.S. Cl. ..................................................... 549/356
[58] Field of Search ......................................... 549/356

[56] References Cited

U.S. PATENT DOCUMENTS

| 2,789,996 | 4/1957 | Schreyer | 558/372 |
| 4,246,177 | 1/1981 | Wu et al. | 549/356 |
| 4,312,717 | 1/1982 | Suzukamo et al. | 546/356 |
| 4,340,544 | 7/1982 | Suzukamo et al. | 549/356 |

OTHER PUBLICATIONS

Chem. Abstracts, vol. 77, 1972-134876p.
J. Amer. Chem. Soc. vol. 77, 4666-4668.
Pet. Chem. USSR (English Translation) 7, (1967), pp. 194-195.

*Primary Examiner*—Glennon H. Hollrah
*Assistant Examiner*—Amelia A. Owens
*Attorney, Agent, or Firm*—Keil & Weinkauf

[57] ABSTRACT

The preparation of 4-methylenetetrahydropyran (I) by reacting 3-methylenepentane-1,5-diol with a sulfohalide in the presence of an aqueous mineral base. Compound I serves as an intermediate in organic syntheses.

4 Claims, No Drawings

PROCESS FOR THE PREPARATION OF 4-METHYLENETETRAHYDROPYRAN

The present invention relates to a novel process for the preparation of 4-methylenetetrahydropyran (I)

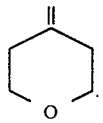

The compound, which is valuable for the synthesis of numerous organic compounds, particularly plant protectants, occurs, for example, as a by-product in the synthesis of isoprene from isobutene and formaldehyde [Chem. Abstr. 77, 134,876 (1971)] or in admixture with isomeric 4-methyl-1-oxa-cyclohex-3-ene (I') in the thermolysis of 4,4-dimethyl-1,3-dioxacyclohexane [Pet. Chem. USSR (Engl. Transl.) 7 (1967) 92].

U.S. Pat. No. 2,789,996 states that this product can be obtained by cyclization of 3-methylenepentane-1,5-diol (II) in the presence of potassium bisulfate. In fact, however, our own tests have shown that this procedure leads to the formation of the isomeric compound 4-methyl-3,6-dihydro-2H-pyran (I') (b.p. 117°–119° C.) only, whilst only traces of compound I are found to be present.

Since the above methods are clearly of little or no use for industrial scale production, it is an object of the inventive to provide a simple, straightforward process for the manufacture of compound I.

Accordingly, we have found a process for the preparation of 4-methylenetetrahydropyran I

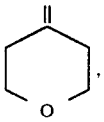

wherein 3-methylenepentane-1,5-diol II

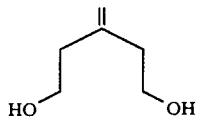

is reacted with a sulfohalide (III) in the presence of an aqueous mineral base.

The starting compound, 3-methylenepentane-1,5-diol (II), is known from the literature and can be obtained by heating paraformaldehyde with isobutene [J. Amer. Chem. Soc. 77, 4,666–4,668 (1955)] or with 3-methyl-but-3-en-1-ol (U.S. Pat. No. 2,789,996).

Our tests have shown that the suitability of a sulfohalide (III) is not dependent on the nature of the acid ester, so that any desired compound of this type can be used, in principle. For economic reasons, however, it will be preferred to use the chlorides of $C_1$–$C_4$-alkanesulfonic acids such as methanesulfochloride and ethanesulfochloride and the chlorides of aromatic sulfonic acids such as benzenesulfonyl chloride, p-toluenesulfonyl chloride, p-chlorobenzenesulfonyl chloride and p-bromobenzenesulfonyl chloride. The amount of sulfochloride used is not critical, but to achieve complete conversion it is advisable to use at least 1 mole and preferably up to 2 moles, per mole of compound II.

The said mineral base serves the purpose of binding the hydrogen halide liberated during the reaction. Particularly suitable bases are, therefore, alkali metal and alkaline earth metal hydroxides and oxides, such as lithium, sodium, potassium and calcium hydroxides and alkali metal and alkaline earth metal carbonates, such as sodium, potassium and calcium carbonates. Sodium or potassium hydroxide is preferably used.

The concentration of mineral base is preferably between 1 and 50% by weight. In order to achieve complete conversion, the amount of base present should be at least equimolar to the amount of diol II, but it is usually advisable to use a molar ratio of base to diol of from 2:1 to 8:1.

Since a two-phase reaction is involved, the additional use of a solvent which is insoluble or sparingly soluble in water is recommended for virtually all cases, in order to increase the volume of the organic phase.

A suitable solvent is, for example, an aliphatic or aromatic hydrocarbon such as pentane, hexane, heptane, cyclohexane, gasoline, petroleum ether, ligroin, benzene, toluene and xylene, a halogenated aliphatic or aromatic hydrocarbon such as methylene chloride, ethylene chloride, carbon tetrachloride, chlorobenzene and o-dichlorobenzene, or an ether such as diethyl or dibutyl ether, diglycoldimethyl ether, tetrahydrofuran and dioxane. A particularly simple variant of the process is furnished by using the end product I as said solvent.

The amount of solvent used is advantageously such that the volume of organic phase equals 10% to 20% of the volume of aqueous phase.

Since inter-reaction of the reactants takes place chiefly at the phase interface, the co-use of a phase transfer catalyst may be advantageous, although it should be remembered that this might in turn promote undesirable saponification of the sulfochloride. Suitable phase transfer catalysts are the conventionally used quaternary ammonium and phosphonium salts, for example triethylbenzylammonium bromide.

The technique of accelerating reactions by phase transfer catalysis, which may readily be applied to the process of the invention, is well known and therefore requires no further description here.

The reaction is preferably carried out at from 20° to 100° C. and more preferably from 80° to 100° C., advantageously by heating under reflux using a solvent of appropriate boiling point.

It is usual to operate at atmospheric pressure. A reduced pressure of, say, from 0.5 to 1 bar, may be advantageous when it is desired to remove the product from the reaction mixture as quickly as possible using a high-boiling solvent, and an elevated pressure of, for example, up to 5 bar may be necessary when a low-boiling solvent is used.

The process of the invention presents no methodical peculiarities, i.e. it can be carried out continuously or batchwise by conventional techniques. Good results are obtained by placing a mixture of the aqueous mineral base, the organic solution of the diol II and any phase transfer catalyst used in a reaction vessel and adding, at reaction temperature, the sulfochloride or a solution thereof.

The reaction mixture may likewise be worked up in conventional manner. However, if the organic phase is separated off, neutralized, washed and dried, it should be remembered that decomposition reactions may take place during subsequent distillation. For this reason it is preferred, in the case of a low-boiling solvent, to distill off the solvent first and then to isolate the desired product as a hetero-azeotrope with water. 4-Methylenetetrahydropyran is obtained in yields of from approx. 60 to 80%.

EXAMPLES 1 to 6

Preparation of 4-methylenetetrahydropyran I

To a mixture of 348 g (3 moles) of 3-methylpentane-1,5-diol, 2,670 g of 30% w/w caustic soda ($\approx$ 20 moles of NaOH) and 100 ml of an organic solvent there were added, at reflux temperature T° C. and over a period of 1 hour, 635 g (3.6 moles) of benzenesulfonic acid, after which the mixture was kept at T° C. for a further 15 minutes before the reaction mixture was worked up to obtain the 4-methylenetetrahydropyran as a hetero-azeotrope with water. Details of the tests and their results are listed in the Table below.

TABLE

| Example | Solvent | T[°C.] | Yield of I [%] |
|---|---|---|---|
| 1 | I | 95–105 | 75 |
| 2 | tetrahydrofuran | 60–70 | 67 |
| 3 | toluene | 90–100 | 63 |
| 4 | methyl-t-butyl ether | 55–65 | 75 |
| 5 | cyclohexane | 75–85 | 66 |

TABLE-continued

| Example | Solvent | T[°C.] | Yield of I [%] |
|---|---|---|---|
| 6* | methyl-t-butyl ether | 55–65 | 78 |

*500 ml of solvent (8 moles of NaOH)

We claim:

1. A process for the preparation of 4-methylenetetrahydropyran (I)

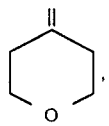

wherein 3-methylenepentane-1,5-diol (II)

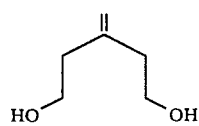

is reacted with a sulfohalide (III) in the presence of an aqueous mineral base.

2. A process as claimed in claim 1, wherein the reaction is carried out in the presence of a solvent which is insoluble or sparingly soluble in water.

3. A process as claimed in claim 1, wherein a phase transfer catalyst is used during the reaction.

4. A process as claimed in claim 1, wherein the sulfohalide (III) used is a $C_1$–$C_4$-alkylsulfochloride or an aromatic sulfochloride.

* * * * *